United States Patent [19]

Dickert et al.

[11] Patent Number: 5,262,732
[45] Date of Patent: Nov. 16, 1993

[54] OIL MONITOR WITH MAGNETIC FIELD

[75] Inventors: Arby D. Dickert; Eric L. Johnson; James F. Kirkpatrick; Keith A. Hawn, both of Knoxville, Tenn.

[73] Assignee: Computational Systems, Inc., Knoxville, Tenn.

[21] Appl. No.: 807,041

[22] Filed: Dec. 11, 1991

[51] Int. Cl.⁵ .................... G01R 27/26; G01N 27/74
[52] U.S. Cl. ................... 324/672; 324/663; 324/686; 324/553; 324/204; 324/232; 73/53.05
[58] Field of Search ............... 324/553, 663, 672, 676, 324/678, 686, 204, 361, 227, 228, 232; 73/53.05

[56] References Cited

U.S. PATENT DOCUMENTS

| | | | |
|---|---|---|---|
| 1,940,772 | 12/1933 | Schoenberg | 88/14 |
| 2,599,583 | 6/1952 | Robinson et al. | 175/183 |
| 2,889,736 | 6/1959 | Borg | 88/14 |
| 3,049,964 | 8/1962 | Miller et al. | 88/14 |
| 3,067,385 | 12/1962 | Rykoskey | 324/663 |
| 3,182,255 | 5/1965 | Hopkins et al. | 324/686 X |
| 3,371,574 | 3/1968 | Dwyer | 88/14 |
| 3,526,127 | 9/1970 | Sarkis | 73/53.05 |
| 3,790,279 | 2/1974 | Skala | 356/70 |
| 3,824,456 | 7/1974 | Wiegand | 324/204 |
| 3,892,485 | 7/1975 | Merritt et al. | 356/103 |
| 4,003,661 | 1/1977 | Yamano | 356/201 |
| 4,029,554 | 6/1977 | Ellison | 204/1 |
| 4,302,754 | 11/1981 | Magee et al. | 340/631 |
| 4,323,843 | 4/1982 | Batham | 324/204 |
| 4,470,008 | 9/1984 | Kato | 324/676 X |
| 4,492,461 | 1/1985 | Jones et al. | 356/38 |
| 4,646,070 | 2/1987 | Yasuhara et al. | 340/603 |
| 4,651,091 | 3/1987 | Chambers et al. | 324/204 |
| 4,677,847 | 7/1987 | Sawatari et al. | 73/64 |
| 4,692,698 | 9/1987 | Lewis | 324/204 |
| 4,701,713 | 10/1987 | Eaton et al. | 324/442 |
| 4,741,204 | 5/1988 | Luck et al. | 73/116 |
| 4,791,374 | 12/1988 | Yodice et al. | 324/439 |
| 4,796,204 | 1/1989 | Inoue | 364/550 |
| 4,831,362 | 5/1989 | Tsaprazis | 340/515 |
| 4,857,829 | 8/1989 | Sagae et al. | 324/61 |
| 4,878,019 | 10/1989 | Tsaprazis et al. | 324/204 |

FOREIGN PATENT DOCUMENTS

| | | | |
|---|---|---|---|
| 2165650 | 4/1988 | United Kingdom | 27/74 |
| 2160655 | 5/1989 | United Kingdom . | |

Primary Examiner—Kenneth A. Wieder
Assistant Examiner—Glenn W. Brown
Attorney, Agent, or Firm—Luedeka, Hodges, Neely & Graham

[57] ABSTRACT

An apparatus for detecting the degree of deterioration in lubricating oil including a grid-like capacitive sensor, that uses the lubricating oil as a dielectric medium, and a magnetic field imposed upon the oil to attract ferromagnetic wear particles into the vicinity of the sensor. Preferably, the magnetic field is generated by a permanent magnet and an electromagnetic aligned such that the magnetic field produced by each magnet acts upon the oil along the same axis.

24 Claims, 5 Drawing Sheets

OIL MONITOR WITH MAGNETIC FIELD

FIELD OF THE INVENTION

This invention relates to an apparatus for detecting the degree of deterioration of lubricating oil and, more particularly, to such an apparatus detecting deterioration due to the following: corrosive products caused by such conditions as oxidation, nitration, and the formation of acids; oil insoluble contaminants such as water and glycol coolants; and ferromagnetic particles caused by system wear.

BACKGROUND OF THE INVENTION

The presence of corrosive products, oil insoluble contaminants or ferromagnetic particles in a lubricating oil can create a threat to the system in which the oil is used because of the unnecessary wear and damage that can occur to the system if the oil is not promptly changed.

Many methods and devices have been developed to detect the contamination or breakdown of oil. One such device, shown in U.S. Pat. No. 4,646,070 issued to Yasuhara, discloses a device for detecting deterioration in lubricating oil which comprises a pair of capacitor electrodes positioned in the lubricating oil. The device uses the oil as a dielectric between the sensors to develop a frequency voltage signal across the sensor capacitor, thus determining the dielectric and deterioration of the oil. A major drawback of this device and others is that they do not inform the tester of the specific type or magnitude of deterioration in the system.

The preferred embodiment of the present invention allows simultaneous testing and identification of corrosive products, contamination, and ferromagnetic wear particles. Thus, since the apparatus detects the type of products present in the oil, a user is able to make a more knowledgeable determination of the conditions causing the deterioration of the oil. Furthermore, the device provides this determination much more economically than laboratory testing. The device also allows multiple tests of the same oil sample because it does not consume the sample during the testing process. Preferably, the device allows testing of the oil outside the system in which the oil is used, thereby allowing the oils of many different systems to be tested by the same device.

SUMMARY OF THE INVENTION

The present invention provides an apparatus for monitoring the condition of lubricating oil preferably for the possible presence of corrosive products, contamination such as water, and ferromagnetic metals in the oil. The apparatus includes containing means for holding the lubricating oil, magnet means for inducing a magnetic field upon the lubricating oil, and sensor means for determining a physical property of the oil in the presence of a magnetic field.

Preferably, the magnet means includes a permanent magnet, an electromagnet and a switching means for changing the polarity of the electromagnet. Thus, both the permanent magnet and the electromagnet simultaneously impose their magnetic fields upon the lubricating oil attracting any ferromagnetic particles in the oil. Furthermore, in the preferred embodiment, the magnetic field of the electromagnet changes polarity over time, alternately reinforcing and canceling the permanent magnetic field, thereby vibrating and reorienting the ferromagnetic particles with the change in the electromagnet's polarity without repulsing the particles away from the sensor.

The sensor means preferably includes a sensor, a means for monitoring the output of the sensor, and a means for processing the sensor's output. The apparatus is assembled in a manner allowing the contained oil to be exposed to the sensor, and the sensor has at least two conductors for which the oil provides an insulating dielectric medium. Thus, the sensor acts as a capacitor and its capacitance varies in relation to at least the area of the conductors, the distance between the conductors, and the dielectric constant and other properties of the oil. This relationship between the sensor and the lubricating oil allows the determination of the properties of the oil as it is influenced by the magnetic field.

In the preferred embodiment, the processing means of the invention determines the amount and type of deterioration in the oil by comparing the capacitance of the sensor when exposed to a test oil sample to the capacitance of the sensor when exposed to a pure calibration sample of the type of oil tested. A higher capacitance in the test oil (relative to the calibration oil) that remains relatively constant over time indicates the presence of corrosive products. A steady increase of the sensor's capacitance while exposed to the test oil indicates the presence of contamination in the oil. A fluctuating increase of the sensor's capacitance while exposed to the test oil indicates the presence of ferromagnetic particles in the oil. The changing polarity of the electromagnet causes the ferromagnetic particles to reorient thereby fluctuating the increase of the sensor's capacitance.

Further details and advantages of this apparatus will become more apparent in the following description and the accompanying drawings.

BRIEF DESCRIPTION OF THE DRAWINGS

The present invention may best be understood by reference to the Detailed Description of a preferred embodiment when considered in conjunction with the Drawings in which.

DETAILED DESCRIPTION OF THE PREFERRED EMBODIMENT

Figure 1:
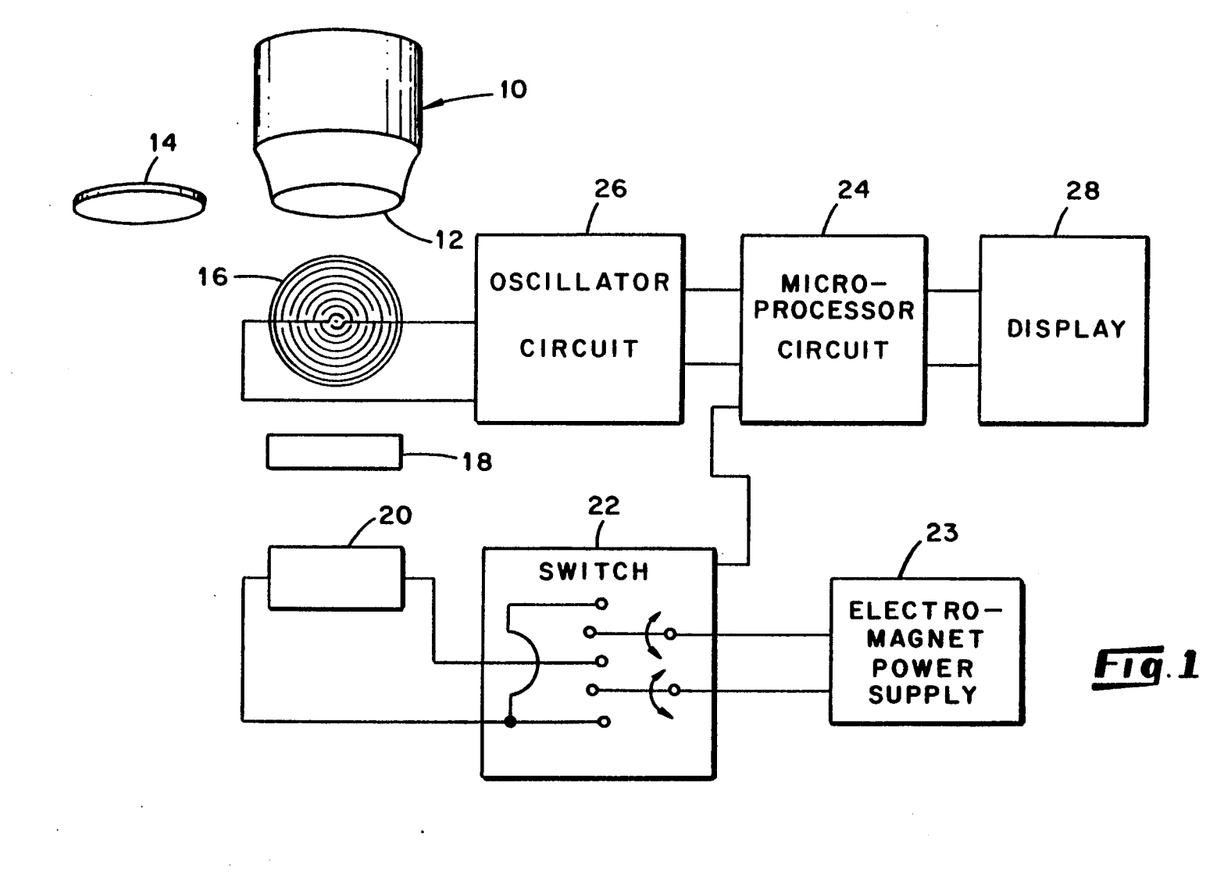
FIG. 1 is a diagrammatical block diagram of a preferred embodiment of the Oil Monitor.

Referring now to the drawings wherein the representations depict the preferred embodiment, there is shown in FIG. 1 a container 10 for holding the sample of lubricating oil that is to be tested. The container has an open mouth 12 and a removable and resealable lid 14 for sealably attaching over the mouth 12. For testing the oil, the container 10 is placed in a measurement position which preferably entails orienting the container 10 vertically with the mouth 12 situated downward so that the mouth 12 covers a horizontally placed sensor 16 thereby allowing the oil to flow down into the sensor 16. The measurement position further allows gravity to influence the oil held in the container 10 thereby causing any contaminants in the oil to migrate toward the sensor 16.

In FIG. 1, the sensor 16 is symbolically represented and is shown removed from the mouth 12 for clarity of illustration. It will be understood that the sensor 16 seals against the mouth 12 to close the container 10 and contain the oil.

A permanent magnet 18 is placed vertically beneath the sensor 16 to allow the magnetic field produced by the permanent magnet 18 to attract any ferromagnetic particles in the oil toward the sensor 16. An electromagnet 20 is located vertically beneath the permanent magnet 18 to allow the magnetic field produced by the electromagnet 20 to act in conjunction or opposition to the permanent magnet 18 depending on the polarity of the electromagnet 20. The electromagnet 20 is electrically connected to switch 22 which is in turn electrically connected to an electromagnet voltage supply 23. The switch 22 and the electromagnet voltage supply 23 allow the electromagnet to be turned on in a north-south orientation, turned on in a south-north orientation, or turned off. The switch 22 in the preferred embodiment is electrically connected to a microprocessor circuit 24 which controls the change in the polarity of the electromagnet 20 as well as the rate at which the electromagnet 20 is turned on and off, which is preferably about one (1) cycle per second. In this embodiment, the electromagnet 20 is a model EMR75 manufactured by Miami Magnet Company operating at 12 volts and about 750 milliamps. The permanent magnet 18 has a diameter of one inch, a thickness of one quarter ($\frac{1}{4}$) inch and a strength that about matches electromagnet 20.

The sensor 16 is electrically connected to an oscillator circuit 26 which uses the sensor 16 as a capacitor to generate an output signal at a frequency corresponding to the capacitance. The oscillator circuit 26 is electrically connected to the microprocessor circuit 24 which uses the generated signal frequency to determine the presence and magnitude of corrosive products, contamination, and ferromagnetic particles in the oil. The microprocessor 24 is electrically connected to the display 28 which outputs the results of the microprocessor's determinations.

Figure 2:
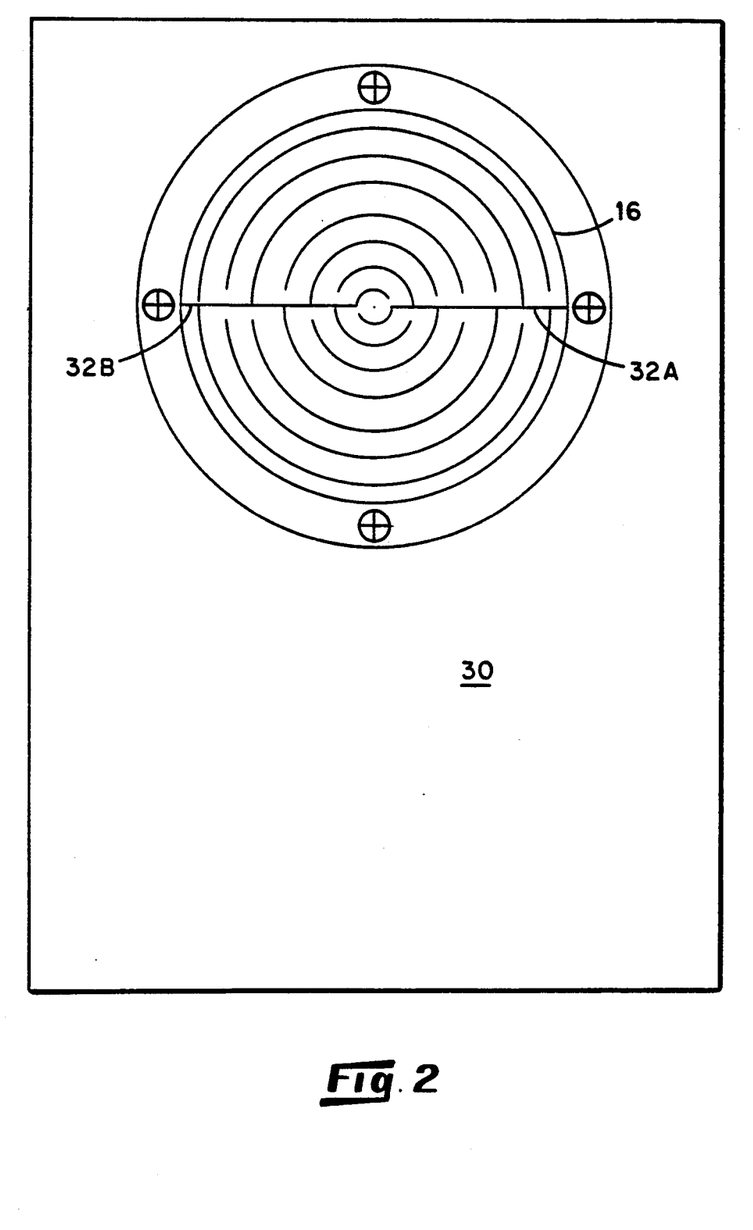
FIG. 2 is a plan view of the Oil Monitor showing the sensor.

FIG. 2 depicts an enlarged, somewhat diagrammatic, top view of the preferred embodiment of the sensor 16 as mounted to the test box 30 which also contains the permanent magnet 18, the electromagnet 20, the switch 22, the electromagnet voltage supply 23, and the oscillator circuit 26 of FIG. 1. The preferred sensor 16 is constructed in a open grid-like formation and is formed from two conductors 32a and 32b having extensions forming concentric half circles. The oil which flows into and adjacent to the sensor acts as the insulating dielectric medium between the conductors 32a and 32b. Thus, the conductors 32a and 32b act as a capacitor plates with the capacitance varying with, at least, the area of the conductors 32a and 32b, the distance between the conductors 32a and 32b, and the dielectric constant of the oil. Numerous capacitance type sensors could be used, but in this embodiment, the sensor has a diameter of about one inch; the conductors 32a and 32b have a diameter of about 250 microns and are spaced apart a distance of about 250 microns; and the sensor 16 has a capacitance in air of about 30 picofarads.

Figure 3:
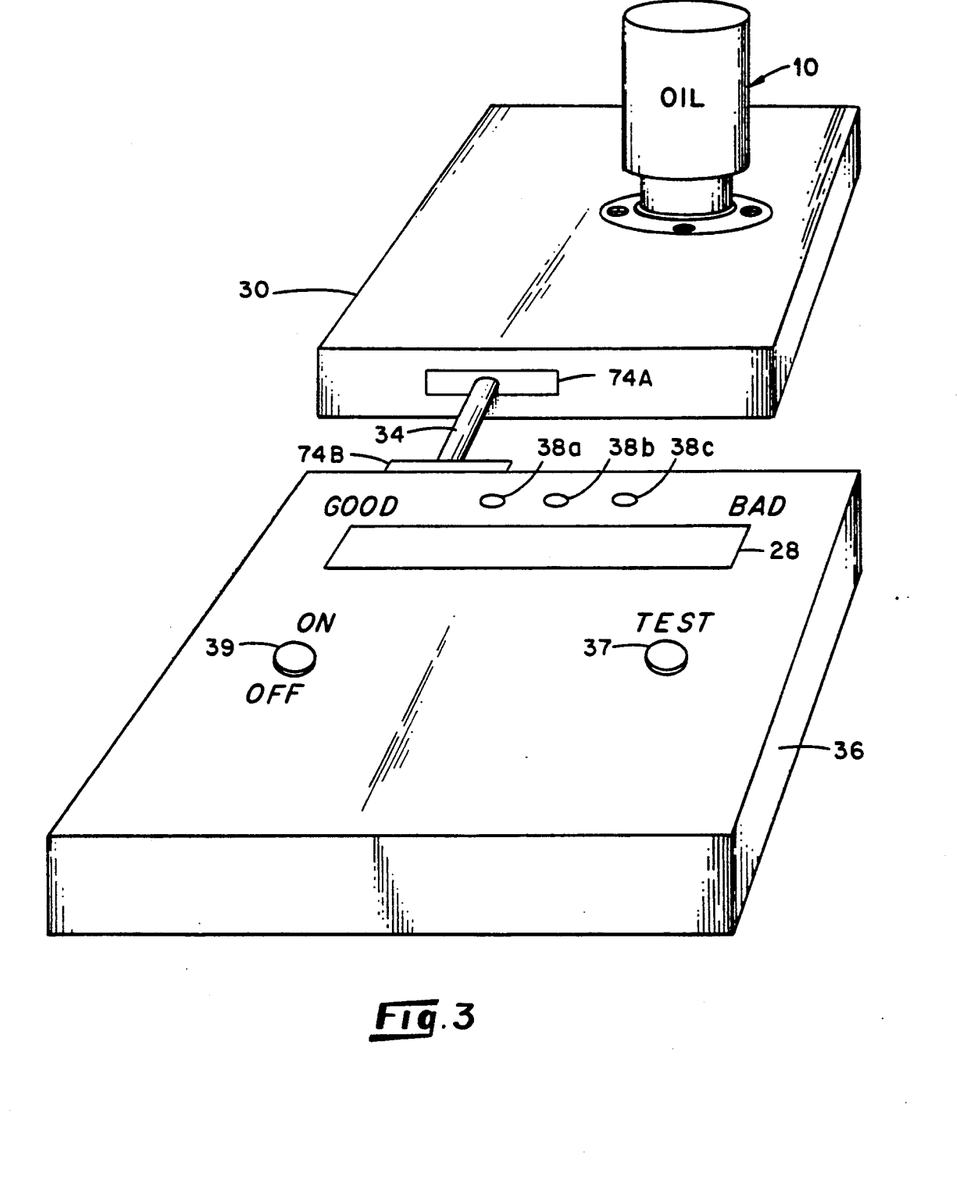
FIG. 3 is a somewhat diagrammatic perspective view of the Oil Monitor.

FIG. 3 depicts an external, somewhat diagrammatic, view of the preferred embodiment of the apparatus. The container 10 is shown in the measurement position on the test box 30. A shielded serial cable 34 electrically connects the components in the test box 30 at connector port 74a to those components in the display box 36 by means of connector port 74b. The display box 36 encloses the microprocessor 24 of FIG. 1. The display 28 is preferably an LCD for displaying the value of contamination, corrosion and ferromagnetic particle levels. The display 28 is mounted on the display box 36 and is electrically connected to the microprocessor 24 within the box. Further depicted are three LEDs, 38a, 38b and 38c, that are electrically connected to the microprocessor 24 within the display box 36 and energized corresponding to the changing levels of corrosion, contamination or ferromagnetic particles.

Figure 4:
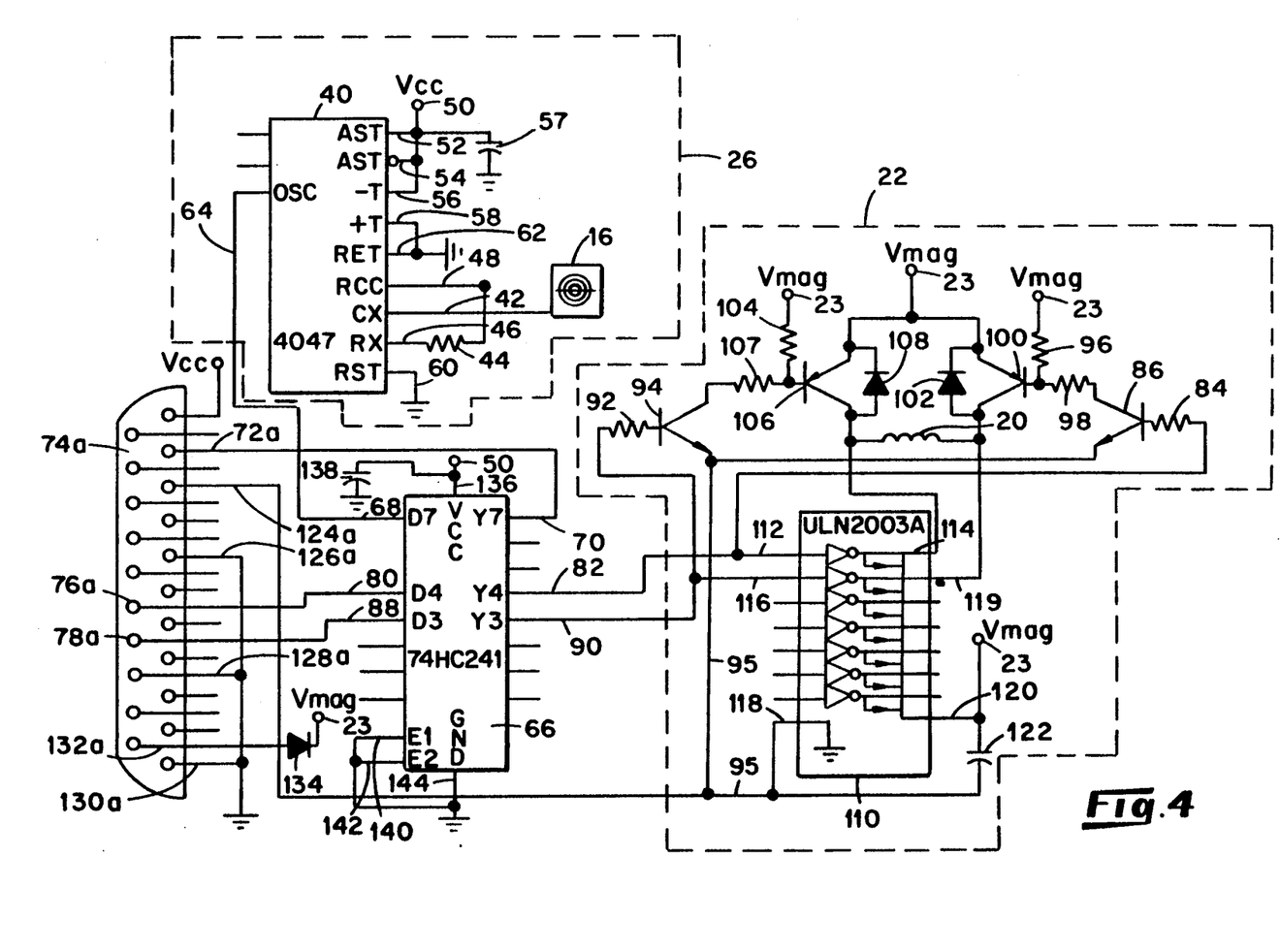
FIG. 4 is a circuit diagram of the sensor and associated analog circuit.

FIG. 4 depicts the preferred embodiment of the internal circuitry of the test box 30 shown in FIG. 3. The oscillator circuit 26 performs the function of generating a frequency pulse based upon the capacitance of the sensor 16. The oil in the sensor 16 acts as the dielectric medium, thereby altering the capacitance of the sensor. The capacitance increases as the dielectric increases (see Formula 1) causing an overall decrease in the frequency produced by the oscillator circuit 26. The presence of polar oxides in the oil causes an increase in the dielectric constant. Additionally, since water has a higher dielectric content than oil, its presence in the oil will cause an increase in the dielectric constant of the oil as the water settles into the vicinity of the sensor 16. If a substantial quantity of water accumulates on the sensor 16, it can cause the sensor 16 to be shorted. The presence of ferromagnetic particles in the oil also causes an increase in the capacitance of the sensor 16 because the accumulation in particles on the sensor increases the sensor's surface area and capacitance in accordance with Formula 1.

Formula 1:

$$C = k^*E^*(A/d)$$

Where: C = the capacitance of the sensor 16; k = the dielectric constant of the oil in the sensor 16; A = the surface area of the sensor 16; and, d = the distance between the sections of the sensor.

The sensor 16 is connected to a pin 42 of a monostable multivibrator 40 and is connected in parallel with the resistor 44 to pin 46 and pin 48 of the monostable multivibrator 40. A constant voltage source 50 is connected to pins 52, 54 and 56 of the monostable multivibrator 40 while pins 58, 60 and 62 are grounded. Pins 52, 54 and 56 are also connected to ground through a, preferably, 0.1 microfarad capacitor 57. Thus, sensor 16 is connected in an R-C circuit to determine the frequency of the signal (pulses) from pin 64. The preferred monostable multivibrator is a general CMOS logic chip Model 4047.

The pin 64 which carries the oscillator signal pulses is connected to a pin 68 of a non-inverting buffer chip 66 which isolates the signal and outputs it from pin 70. The pin 70 is connected to a pin 72a of a connector port 74a. A signal is thereby sent through the connector port 74a along the serial cable 34 of FIG. 3 to an identical connector port 74b of the display box 36 of FIG. 3.

The connector port 74a also receives signals from the microprocessor 24 from pins 76a and 78a of the connector port 74a. These signals control the switch 22 for changing the polarity of the electromagnet 20 and for turning the electromagnet 20 on or off. As the permanent magnet 18 continuously attracts ferromagnetic particles onto the surface of the sensor 16, the electromagnet, when turned on in opposition to the permanent magnet 18, will cause the particles on the sensor to shift thereby changing the surface area of the sensor which results in an altered frequency output from the monostable multivibrator 40. Thus, the electromagnet will cause a fluctuation in output pulses as its polarity is changed if ferromagnetic particles are present in the oil. In the preferred embodiment, an electromagnet is employed for shifting the ferromagnetic particles in the vicinity of the sensor, but it will be understood by those of ordinary skill in the art that a similar effect could be produced by a movable permanent magnet that could be shifted or rotated to change the magnetic field. Furthermore, in the preferred embodiment, the electromagnet's polarity is reversed to produce the maximum fluctuation while continuously attracting particles with the permanent magnet 18. Persons knowledgeable in the art will further understand that total reversal of the polarity of the electromagnet is not required.

The pin 76a of connector port 74a is connected to a pin 80 of the buffer chip 66 which isolates the switching signal and outputs it from pin 82. The pin 82 is connected in series with a resistor 84 to the base of an NPN transistor 86. The pin 78a of connector port 74a is connected to pin 88 of the buffer chip 66 which isolates the signal and outputs it from the pin 90. The pin 90 is connected in series with a resistor 92 to the base of an NPN transistor 94. The emitters of the transistors 86 and 94 are tied together and attached to a signal ground wire 95 which acts to reduce noise in the system. The collector of transistor 86 is connected in series through resistors 96 and 98 to the electromagnet power supply 23, which provides $V_{mag}$, and further connected through resistor 98 to the base of a PNP transistor 100. A diode 102 is coupled across the emitter and collector of transistor 100 thus acting as a protection device for transient relief. The emitter of transistor 100 is further connected to the electromagnet voltage supply 23, and the collector of transistor 106 is further coupled to the electromagnet 20. The collector of transistor 94 is connected in series to the electromagnet power supply 23 through resistors 104 and 107 and is further connected to the base of a PNP transistor 106 through resistor 107. A diode 108 is coupled across the emitter and collector of transistor 106 thus acting as a protection device for transient relief. The emitter of transistor 106 is further connected to the electromagnet voltage supply 23 (preferably a battery), and the collector of transistor 106 is further connected to the electromagnet 20.

The pin 82 of the buffer chip 66 is also coupled with a pin 112 of a Darlington driver chip 110 which operates as a current sink, dependent upon the logic level, and is connected from pin 114 to the electromagnet 20 in conjunction with the collector of transistor 106. The pin 90 of buffer chip 66 is connected to a pin 116 of the driver chip 110 which is in turn coupled from pin 118 to the electromagnet 20 in conjunction with the collector of the transistor 100. This configuration allows the current flow to the electromagnet 20 to be alternated or shut off completely by the microprocessor 24 thus providing the switch 22.

The driver chip 110 is connected to the signal ground wire 95 through a pin 118 and is connected to the electromagnet voltage supply 23 through a pin 120 which is further coupled through a series capacitor 122 to the signal ground wire. The signal ground wire 95 is connected to pin 124a of the connector port 74a.

The connector port 74a has pins 126a, 128a, and 130a connected to ground and has pin 132a connected through a diode 134 to the electromagnet power supply 23.

The buffer chip 66 has pin 136 connected to the constant voltage source 50 which is in turn coupled to ground through capacitor 138. The buffer chip also has pins 140, 142 and 144 coupled to ground.

Figure 5:
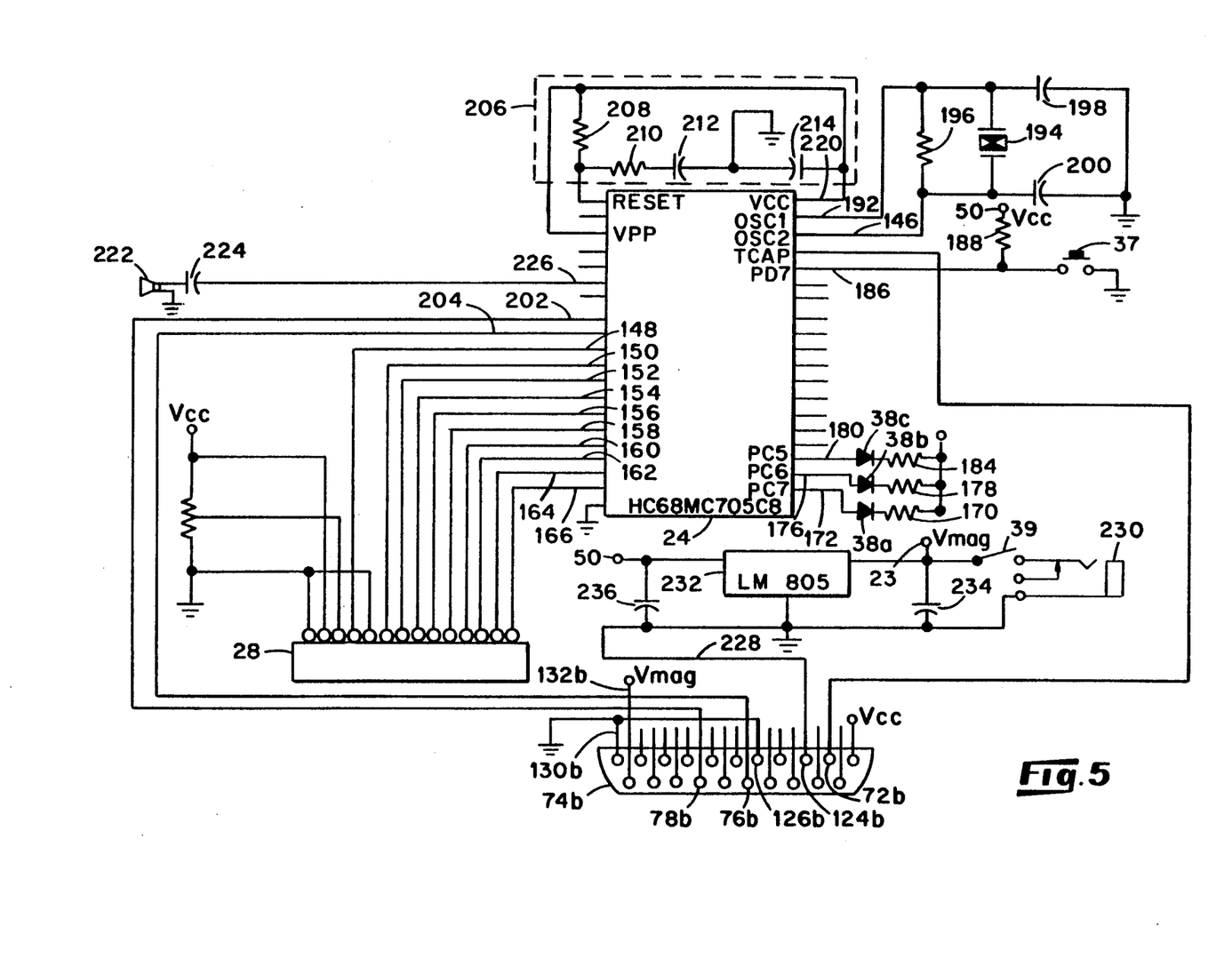
FIG. 5 is a circuit diagram of the microprocessor and associated circuitry that monitors the sensor and produces an output.

FIG. 5 depicts the internal circuitry of the display box 36 of FIG. 3. The connector port 74b connects the test box 30 to the shielded serial cable 34. The pin 72b carries the oscillator pulse and is connected to the microprocessor 24 at pin 146. The preferred microprocessor is an HCMoss microcontroller unit model MC68HC705C8 with erasable programmable read only memory. The microprocessor 24 counts the frequency pulses produced by the multivibrator 40 to determine the amount of contamination, corrosive products and ferromagnetic particles in the test oil.

Upon initial application of power to the microprocessor 24, the microprocessor 24 is set in calibration mode whereby it stores certain calibration counts for use in the test mode. The calibration mode stores certain values which will be used as the "normal" values for the oil to be tested. These values are obtained from running the calibration sequence upon an unused sample of the oil. The calibration sequence is similar to the test sequence. To perform the calibration sequence, the calibration oil is put into the container 10, and the container is placed in measurement position.

The microprocessor then begins receiving and counting the pulses output from the monostable multivibrator 40. Pulse counts are made when the electromagnet is turned on in north-south polarity, turned on in south-north polarity, and turned off. In the preferred embodiment, these three count readings constitute one cycle.

The mean calibration value, $M_c$, is determined over a number of cycles, preferably, twenty cycles, and, preferably, the first ten of which are counted and ignored. During each cycle between ten and twenty cycles, the pulse count is stored while the electromagnet is off, and the mean value of the stored pulse counts is stored as $M_c$. The number of cycles used to determine $M_c$ is a matter of design choice, but it is preferred to ignore the first few cycles and then determine an average based on a number measurements taken over a number of cycles.

After the twenty-first cycle, the pulse count when the electromagnet is off is stored as the magnet-off calibration value $OFF_c$. Furthermore, the difference between the electromagnet when off and when on in north-south polarity is stored $N_c$ and the difference between the electromagnet when off and when on in south-north polarity is stored $S_c$. After these calibration values are stored, the microprocessor 24 reconfigures and resets its internal flags for test mode. Since the values obtained in the calibration mode are used as the "normal" values for the oil, a poor calibration oil will cause the test sequence to produce improper results.

The test mode is run by filling the container 10 with the test oil and placing the container in measurement position. The microprocessor 24 then begins running test cycles. After twenty cycles (preferably) have been run in the test mode, the microprocessor 24 stores the mean pulse count obtained between the tenth and the twentieth cycles (preferably) when the electromagnet is turned off as the mean test value $M_T$. This mean value $M_T$ is subtracted from the similarly obtained calibration value $M_c$ and the difference is output to the LCD display 28 as the corrosion index R.

Formula 2:

$$R = M_c - M_T$$

Thus, if the test oil contains no corrosion, the mean values obtained in the test and calibration mode will be approximately the same, giving a corrosion index R of approximately zero.

After the twenty-first cycle (preferably), the microprocessor 24 subtracts the pulse count taken when the electromagnet is turned off (the magnet-off test value $OFF_T$) from the mean test value $M_T$, and the difference between the magnet-off calibration value $OFF_c$ and the mean calibration value $M_c$ is further subtracted. The resultant value is outputted to the LCD display 28 as the contamination index C.

Formula 3:

$$C = (M_T - OFF_T) - (M_c - OFF_c)$$

This value is updated similarly each cycle using the new magnet off test value $OFF_T$ for each cycle. This method of determining the contamination allows any pulse offsets due to corrosion to be disregarded. Furthermore, the testing for contamination during each cycle allows for the time that it takes for gravity to draw the contaminants into the vicinity of the sensor 16. Beginning at the twenty-first cycle, the difference between the pulse count when the electromagnet 20 is off and the pulse count when the electromagnet 20 is on is determined. This determination is made for the difference when the electromagnet is in both polarities and stored as $N_T$ and $S_T$. Similar values obtained from the calibration mode are then subtracted from the test mode values with the resultant values outputted to the LCD display 28 as the ferromagnetic debris index $F_x$.

Formula 4:

$$F_x = (N_c - N_t) + (S_c - S_t)$$

A similar value is then obtained in succeeding cycles and added to the previous value so that a running total is obtained and displayed.

Formula 5:

$$F_{TOT} = F_x + F_{x+1}$$

Thus, the amount of ferromagnetic debris in the oil is indicated.

The microprocessor 24 uses pins 148, 150, 152, 154, 156, 158, 160, 162, 164 and 166 to output the index values to the display 28. In the preferred embodiment, LEDs are used as a further indicator of the condition of the oil. The microprocessor 24 sends a signal to a green LED 38a, which is tied to the constant voltage source 50 through a resistor 170. The signal is sent from pin 172 thereby energizing the green LED 38a. If the corrosion index, the contamination index or the ferromagnetic debris index increases to a significant level, the green LED 38a is de-energized and the yellow LED 38b is energized by a signal from pin 176 of the microprocessor 24 to indicate the need for caution because of a borderline oil sample. The yellow LED 38b is connected to the constant voltage source 50 through a resistor 178. If any of the index values increase to a "high" reading (determined by the designer according to the anticipated application of the device), the yellow LED 38b is de-energized and the microprocessor sends a signal through a pin 180 to energize a red LED 38c, which connected to the constant voltage source 50 through a resistor 184, to thereby indicate that the oil sample is "bad." In the event that a pulse count reading produced by the sensor for any condition of electromagnet 20 drops to a level that would indicate a shorting of the sensor due to large amounts of water or debris, the red LED 38c will be pulsed and the word "CRITICAL" will be sent to the display 28.

In the preferred embodiment, the microprocessor 24 receives the pulse counts for 100 cycles and then stops if the contamination index and the ferromagnetic debris index values remain very small. However, if the contamination or ferromagnetic debris indicates an appreciable amount of deterioration in the oil, the microprocessor continues receiving for 256 cycles to determine the full amount of the contaminants. The word "FINISHED" will be sent to the display 28 when the microprocessor 24 completes its readings.

The microprocessor checks for a high reading on pin 186 to determine if the test should be aborted. Aborting occurs by pressing the test button while in test mode. The pin 186 is connected to the constant voltage source 50 through a resistor 188 and to the test button 37 which connects to ground when pressed, thereby allowing the line to be driven high.

The microprocessor controls the polarity and the power to the electromagnet 20 by output signals from pins 202 and 204 which are connected to pins 76b and 78b of the connector port 74b. Thus, the signals are transferred along the shielded serial cable 34 to the connector port 74a of the test box 30. A low signal generated on both pins 202 and 204 will force the electromagnet 20 into its "off" mode. A high signal generated upon pin 202, while a low signal is generated on 204, will force the electromagnet into the "on" mode in north-south polarity. Finally, a high signal generated upon pin 204, while a low signal is generated on pin 202, will force the electromagnet into the "on" mode in south-north polarity.

A reset circuit 206 including resistors 208 and 210 connected to capacitors 212 and 214 is attached to the constant voltage source 50 and acts to pull up the input voltage to five volts after the supply contact is made. The reset circuit 206 is attached to pins 216, 218 and 220 of the microprocessor 24, thereby assuring that the internal reset of the microprocessor is working properly.

In the preferred embodiment, a beeper alarm 222 is used for signaling the presence of dangerous levels of deterioration and contamination in the test oil. The beeper 222 is attached through a capacitor 224 to a pin 226 of the microprocessor 24.

The connector port 74b has a pin 124b connected to a probe ground wire 228 which is connected to a power clip 230 for hook up to an external power source. The switch 39 engages the external power source when depressed thereby powering the electromagnet voltage supply 23. The switch 39 is further connected to a voltage regulator 232 which regulates the voltage to five volts for supplying the constant voltage source 50 which powers the digital requirements of the system. The electromagnet voltage supply 23 is connected to the probe ground wire 228 through resistor 234, and the constant voltage source 50 is similarly connected to the ground wire 228 through resistor 236.

The connector port 74b has pins 126b and 130b connected to ground. The connector port 74b further has pin 132b connected to the electromagnet voltage supply 23.

Although a preferred embodiment is described herein, it will be understood that the invention is capable of numerous modifications, rearrangements and substitutions of parts without departing from the scope of the invention as defined in the Claims.

We claim:

1. An apparatus for monitoring the condition of and detecting a physical property of contaminants in a sample of lubricating oil comprising:
   a. containing means for holding and confining the sample of lubricating oil, said containing means defining a substantially sealed chamber when in place in said apparatus and the sample of lubricating oil being substantially stagnant within said containing means;
   b. magnet means for inducing a magnetic field upon the sample of lubricating oil in said containing means and for causing the migration of any magnetically responsive contaminants within the stagnant oil sample;
   c. sensor means located in the magnetic field for sensing a physical property of the stagnant oil sample in the presence of the magnetic field and for generating a sensor signal corresponding to the value of the physical property sensed; and
   d. analysis means having as input said sensor signal for sampling said sensor signal at discrete time intervals, determining the presence and type of contaminants in said lubricating oil, and determining the condition of said lubricating oil based upon the value of the sensor signal and the change in said sensor signal over said discrete time intervals.

2. The apparatus as defined in claim 1 wherein said magnet means comprises a permanent magnet.

3. The apparatus as defined in claim 1 wherein said magnet means comprises an electromagnet.

4. The apparatus as defined in claim 1 wherein:
   said magnet means comprises a permanent magnet located relative to said sensor means for imposing a constant magnetic field on the oil proximate said sensor means; and
   said sensor means comprises a sensor having at least two conductors exposed to the lubricating oil that provides an insulating dielectric medium between said conductors to form a capacitor.

5. The apparatus as defined in claim 1 further comprising:
   a calibration oil;
   a test oil; and
   said sensor means producing a signal corresponding to physical properties of oil to which it is exposed, producing and storing calibration signals when exposed to said calibration oil, producing and storing test signals when exposed to said test oil, and determining a corrosion index corresponding to corrosion of the sample of oil based on a comparison of at least one said test signal to at least one said calibration signal.

6. The apparatus as defined in claim 1 wherein said sensor means generates a signal corresponding to physical properties of the oil, said sensor means further comprising processor means responsive to said signal for determining a contamination index based upon change of the signal over time.

7. The apparatus as defined in claim 1 wherein said sensor means comprises a sensor having at least two conductors exposed to the lubricating oil that provides an insulating dielectric medium between said conductors to form a capacitor.

8. The apparatus as defined in claim 1 wherein said sensor means comprises a sensor and monitor means for monitoring the output from said sensor.

9. The apparatus as defined in claim 1 wherein said sensor means comprises:
   a sensor;
   monitor means for monitoring the output from said sensor; and
   processing means for interpreting the output from said monitoring means.

10. The apparatus as defined in claim 1 wherein said sensor means comprises:
    a sensor; and
    monitor means for monitoring the output from said sensor, said sensor having at least two conductors exposed to the lubricating oil that provides a dielectric medium between said conductors to form a capacitor.

11. An apparatus for monitoring the condition of lubricating oil comprising:
    a. containing means for holding a sample of the lubricating oil;
    b. magnet means for inducing a magnetic field upon the oil sample in said containing means;
    c. sensor means located in the magnetic field for sensing a physical property of the oil sample in the presence of the magnetic field; and wherein said magnet means further comprises;
    d. a permanent magnet located relative to said sensor means for imposing a constant magnetic field on the oil and for attracting particles in the oil toward the sensor means;
    e. an electromagnet located relative to said sensor means for imposing a pulsed magnetic field on the oil proximate to said sensor means;
    f. an electric power source electrically connected to said electromagnet; and
    g. switching means electrically connected between said power source and said electromagnet for alternating the polarity of said electromagnet.

12. An apparatus for monitoring the condition of lubricating oil comprising:
    a. containing means for holding a sample of the lubricating oil;
    b. magnet means for inducing a magnetic field upon the oil sample in said containing means;
    c. sensor means located in the magnetic field for sensing a physical property of the oil sample in the presence of the magnetic field;
    said magnet means includes an electromagnet and a switching means for changing the polarity of said electromagnet; and
    said sensor means includes a sensor having at least two conductors exposed to the lubricating oil that provides an insulating dielectric medium between said conductors to form a capacitor.

13. The apparatus as defined in claim 12 wherein said magnet means further comprises a permanent magnet.

14. An apparatus for monitoring the condition of lubricating oil comprising:

a. containing means for holding a sample of the lubricating oil;
b. magnet means for inducing a magnetic field upon the oil sample in said containing means;
c. sensor means located in the magnetic field for sensing a physical property of the oil sample in the presence of the magnetic field; and
said magnet means further comprising an electromagnet and switching means for altering said magnetic field generated by said electromagnet.

15. The apparatus as defined in claim 14 wherein said magnet means further comprises a permanent magnet, said permanent magnet and said electromagnet both being located for imposing a magnetic field on the lubricating oil proximate to said sensor means.

16. The apparatus as defined in claim 14 wherein, said sensor means generates a signal corresponding to physical properties of the oil, and said sensor means further comprises processor means responsive to said signal for determining a magnetically responsive debris index based upon change of the signal when the switching means alters the magnetic field.

17. An apparatus for monitoring the condition of and detecting at least one physical property of contaminants in a sample of lubricating oil comprising:
a. a container for holding and confining the oil sample, said container having an opening, defining a substantially sealed chamber when in place in said apparatus and the oil sample being substantially stagnant within the container;
b. A sensor having at least two conductors, said sensor configured for covering the opening of said container and for being disposed below the container in a measurement position such that said lubricating oil flows into the sensor and becomes at least part of the insulating dielectric medium between said conductors, said conductors, when exposed to the lubricating oil, forming a capacitor which as a capacitance that varies in relation to at least the area of the conductors, the dielectric constant of the lubricating oil and the distance between the conductors;
c. a permanent magnet located proximate to said sensor for imposing a constant magnetic field on the oil;
d. an electromagnet located proximate to said sensor for imposing a pulsed magnetic field on the oil, said constant and pulsed magnetic fields for causing the migration of magnetically responsive contaminants to said sensor and said pulsed magnetic field further for varying the orientation of magnetically responsive contaminants;
e. monitor means for monitoring the capacitance of said sensor at discrete time intervals and determining the condition of and at least one physical property of contaminants in the oil sample based upon the capacitance of said sensor and the change in capacitance of said sensor over said discrete time intervals;
f. an electric power source electrically connected to said electromagnet; and
g. switching means electrically connected between said power source and said electromagnet for alternating the polarity of said electromagnet.

18. An apparatus for determining the possible presence of corrosive products, ferromagnetic particles and contamination in lubricating oil comprising:

a. a container for holding said lubricating oil, said container including a bottle having an open mouth and a removable and resealable lid for sealably attaching to the mouth;
b. a sensor having at least two ferromagnetic conductors disposed in a spaced apart side-by-side relationship in a grid-like formation, said sensor configured for being disposed below the container in a measurement position such that said lubricating oil flows into the sensor and becomes an insulating medium between said conductors, said a conductors, when exposed to the lubricating oil, forming a capacitor which has a capacity that varies in relation to at least the area of the conductors, the dielectric constant of the lubricating oil and the distance between the conductors;
c. a permanent magnet located proximate to said sensor for imposing a constant magnetic field on the oil in the vicinity of the sensor and attracting ferromagnetic particles int eh oil toward the sensor;
d. an electromagnetic having a magnetic field of lesser intensity than said permanent magnet, said electromagnet located proximate to said sensor for imposing a pulsed magnetic field on the oil in the vicinity of the sensor and for reorienting ferromagnetic particles in the oil;
e. an electric power source electrically connecting said electromagnet;
f. switching means electrically connected between said power source and said electromagnet for alternating the polarity of said electromagnet at a preselected switching frequency;
g. monitor means for monitoring the capacitance of said sensor and producing a capacitance signal corresponding to the capacitance; and
h. processing means for determining the level of corrosive products in the lubricating oil based upon the capacitance of said sensor, determining the contamination in the lubrication oil based upon a change in the capacitance of the sensor caused by change in the pulsed magnetic field.

19. An apparatus for determining the presence of magnetically non-responsive contaminants which will migrate due to the influence of gravity in used lubricating oil samples comprising:
container means for holding and confining the oil sample, said containing means defining a substantially sealed chamber when in place in said apparatus and the sample of lubricating oil being substantially stagnant within said containing means;
sensor means for capacitively sensing the presence of contaminants in the stagnant oil sample and generating a sensor signal corresponding to the contaminants present in the stagnant oil sample; and
monitor means having said sensor signal as input for monitoring said sensor means, sampling said sensor signal at a first time to produce a first measurement, waiting for a delay period of time, then sampling said sensor signal at at least a second time to produce a second measurement, and determining at least one physical property of contaminants in the oil based on the first and second measurements and the change in said measurements over the delay period.

20. The apparatus of claim 19 wherein said sensor means further comprises a capacitive sensor disposed in contact with the oil sample.

21. The apparatus of claim 19 wherein said monitor means samples said sensor signal after the contaminants in the oil sample have been allowed to migrate for a delay period of time of about five minutes.

22. The apparatus of claim 19 wherein said monitor means makes at least one intermediate sample of said sensor signal before the contaminants in the oil sample have migrated less than about 5 minutes and at least one final sample after the contaminants in the oil sample have been allowed to migrate for a period of time of about five minutes.

23. The apparatus of claim 19 wherein said monitor means samples said sensor signal a plurality of times at a uniform rate over a predetermined delay period of time.

24. The apparatus of claim 19 wherein said monitor means sample said sensor signal at a rate of one sample per second for a total of about 256 samples.

* * * * *